United States Patent [19]
Liu et al.

[11] Patent Number: 5,756,473
[45] Date of Patent: May 26, 1998

[54] 6-O-METHYL ERYTHROMYCIN D AND PROCESS FOR MAKING

[75] Inventors: Jih-Hua Liu, Green Oaks; Joseph E. Celebuski, Gurnee, both of Ill.

[73] Assignee: Abbott Laboratories, Abbott Park, Ill.

[21] Appl. No.: 560,753

[22] Filed: Nov. 21, 1995

[51] Int. Cl.⁶ .......................... C07H 17/08; A61K 31/70
[52] U.S. Cl. .................................. 514/29; 536/7.2
[58] Field of Search .................. 536/7.2; 514/29

[56] References Cited

U.S. PATENT DOCUMENTS

| | | | |
|---|---|---|---|
| 4,331,803 | 5/1982 | Watanabe et al. | 536/7.2 |
| 4,496,546 | 1/1985 | Celmer et al. | 514/29 |
| 4,672,109 | 6/1987 | Watanabe et al. | 536/7.2 |

FOREIGN PATENT DOCUMENTS

| | | |
|---|---|---|
| 0080818 | 8/1983 | European Pat. Off. |
| 0080818A | 5/1992 | European Pat. Off. |

OTHER PUBLICATIONS

Journal of Antibiotics, vol. 43 (1990), pp. 544–549, S. Morimoto, et al., "Chemical Modification of Erythromycins".

Primary Examiner—Elli Peselev
Attorney, Agent, or Firm—Mona Anand; Thomas D. Brainard

[57] ABSTRACT

An antibacterial compound is disclosed having the formula:

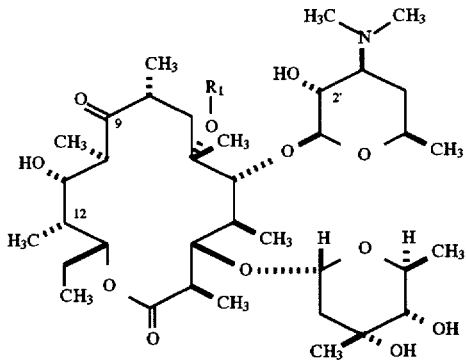

wherein $R_1$ is loweralkyl or a pharmaceutically acceptable salt, ester or prodrug thereof, processes and intermediates useful in the preparation of the above compounds, as well as compositions containing the same and methods for their use.

11 Claims, No Drawings

6-O-METHYL ERYTHROMYCIN D AND PROCESS FOR MAKING

TECHNICAL FIELD

The present invention relates to novel semi-synthetic 6-O-alkyl macrolides having antibacterial activity and useful in the treatment and prevention of bacterial infections. More particularly, the invention relates to a 6-O-methyl derivative of erythromycin D, processes for its preparation, compositions containing such compound and methods for using the same.

BACKGROUND OF THE INVENTION

Erythiromycins A through D, represented by formula (I),

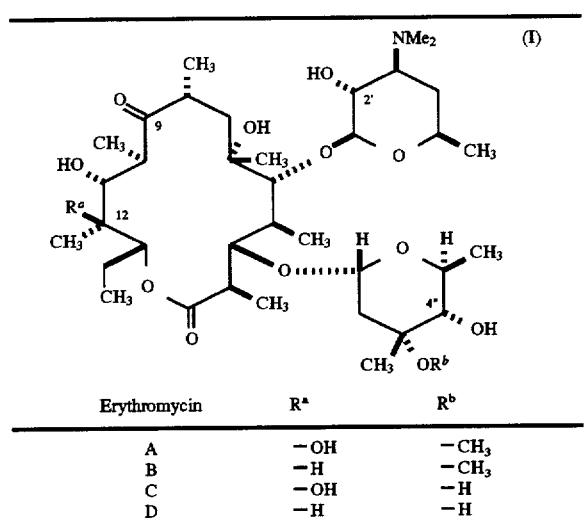

| Erythromycin | R$^a$ | R$^b$ |
|---|---|---|
| A | —OH | —CH$_3$ |
| B | —H | —CH$_3$ |
| C | —OH | —H |
| D | —H | —H | are well-known and potent antibacterial agents. Erythromycin A in particular is widely used to treat and prevent bacterial infection. As with other antibacterials, however, bacterial strains having resistance or insufficient susceptibility to erythromycin have been identified. Consequently, numerous investigators have prepared chemical derivatives of erythroienycin in an attempt to obtain analogs having modified or improved profiles of antibiotic activity.

The 6-O-methyl derivative of erythromycin A was disclosed in U.S. Pat. No. 4,331,803, published May 25, 1982 which is incorporated herein by reference. U.S. Pat. No. 4,672,109, published Jun. 9, 1987, discloses a method for the selective methylation of the 6-hydroxy group of erythromycin A via 9-oxime derivatives to give 6-O-methylerythromycin A 9-oximes. The preparation of 6-O-methylerythromycin A 9-oxime was also disclosed in U.S. Pat. No. 4,670,549, published Jun. 2, 1987. The conversion of 6-O-methylerythromycin A 9-oximes to 6-O-methylerythromycin A was disclosed in Japanese Patent No. 95055958, published Jun. 14, 1995. The preparation of erythromycin D by fermentation was disclosed in U.S. Pat. No. 4,496,546, published Jan. 29, 1985, which is incorporated herein by reference.

SUMMARY OF THE INVENTION

The present invention comprises novel 6-O-alkyl derivatives of erythromycin D having the formula:

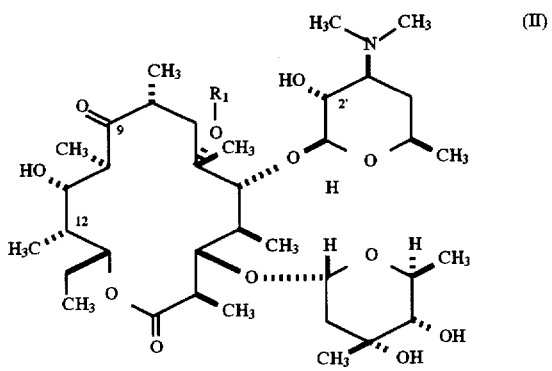

wherein $R_1$ is loweralkyl, or a pharmaceutically acceptable salt, ester or prodrug thereof.

In a preferred embodiment of formula II, $R_1$ is methyl.

The present invention also comprises processes for the preparation of the compounds of the invention, as well as novel intermediates useful therein which have the formula:

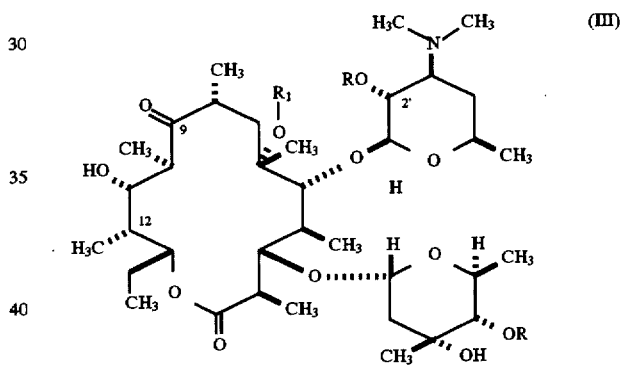

wherein R is preferably the same hydroxy protecting group and $R_1$ is hydrogen or loweralkyl.

A preferred process for the preparation of a compound of the formula:

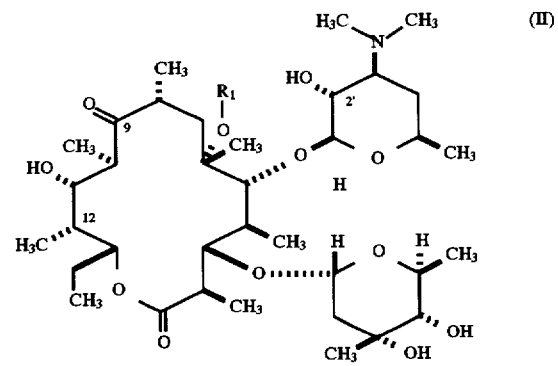

wherein $R_1$ is loweralkyl comprises treating a compound of the formula:

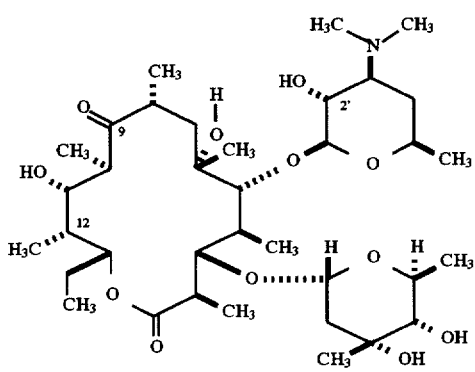

with an hydroxy protecting reagent typically selected from acid anhydrides or acid chlorides such as acetic anhydride or propionyl chloride or benzyl bromide in the presence of a base typically selected from group I or group II metal hydroxides or carbonates or an organic base, such as potassium hydroxide, sodium hydroxide, lithium hydroxide or pyridine to give a compound of the formula:

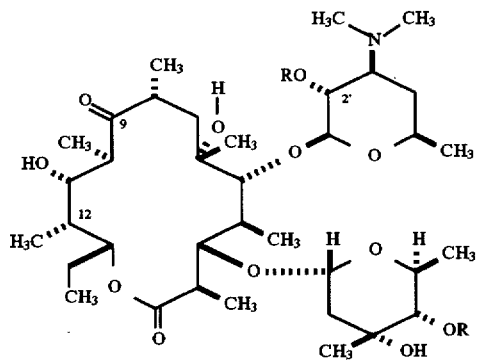

wherein R is acetyl, propionyl or benzyl;

treating said compound with an alkylating agent typically selected from the group consisting of methyl iodide, methyl bromide, methyl p-toluenesulfonate, methyl methanesulfonate, dimethyl sulfate, ethyl iodide, ethyl bromide, ethyl p-toluenesulfonate, ethyl methanesulfonate, and diethyl sulfate to give a compound of the formula:

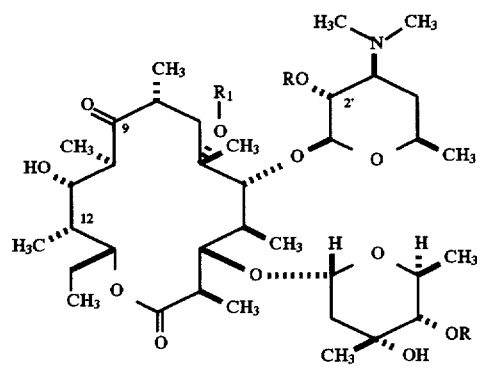

wherein $R_1$ is methyl or ethyl and R is an hydroxy protecting group such as acetyl, propionyl or benzyl; and treating said compound with ethanolic or methanolic potassium carbonate, sodium hydroxide, lithium hydroxide or potassium hydroxide or catalytic hydrogenation in the case of a benzyl protecting group.

In a more preferred process, $R_1$ is hydrogen or methyl.

In a more preferred process, each R is acetyl.

In an even more preferred process, $R_1$ is hydrogen or methyl and R is acetyl.

The present invention further comprises the use of 6-O-loweralkyl erythromycin D as an intermediate in the preparation of 6-O-loweralkyl erythromycin A.

Because of its antibacterial activity, it is anticipated that the compound of the present invention will be useful as pharmaceutical agent or industrial disinfectant. Accordingly, the invention also comprises compositions useful in the treatment and prevention of bacterial infection, comprising a therapeutically effective amount of a compound of formula (II) in combination with a pharmaceutically acceptable carrier.

The invention further comprises a method for treating and preventing bacterial infections in humans and other animals, comprising administering to a patient in need of such treatment a therapeutically effective amount of a compound of the invention for such time as is necessary to achieve the desired therapeutic effect.

DETAILED DESCRIPTION OF THE INVENTION

The present invention comprises a novel derivative of erythromycin having the formula:

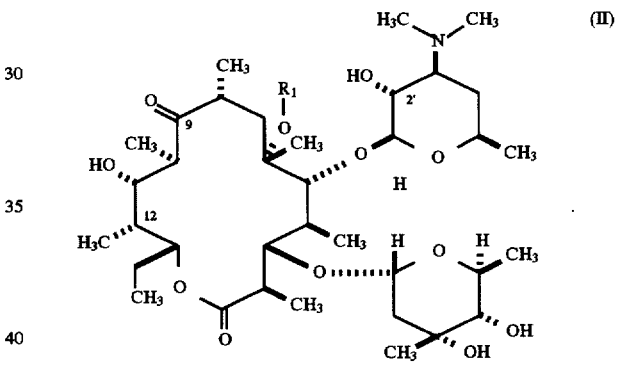

wherein $R_1$ is loweralkyl, preferably methyl;
or a pharmaceutically acceptable salt, ester or prodrug thereof.

In a second aspect of the present invention is a process for preparing the compounds of the invention as well as intermediates useful in their preparation. Such intermediates (compounds 3, 4, 7 and 8) are shown in Schemes I and II.

Yet another aspect of the present invention comprises the use of 6-O-loweralkyl erythromycin D as intermediates in the preparation of 6-O-loweralkyl erythromycin A, and in particular the use of 6-O-methylerythromycin D as an intermediate in the preparation of 6-O-methylerythromycin A.

The term "hydroxy-protecting group" or "O-protecting group" as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)), which is incorporated herein by reference. O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The term "hydroxy-protecting reagent" as used herein refers to those reagents which react with the hydroxy functionality to give the hydroxy protected groups described above. For example, the hydroxy-protecting reagent acetic anhydride affords the acetyl hydroxy-protecting group. These reagents are described in Greene, "Protective Groups In Organic Synthesis," (John Wiley & Sons, New York (1981)).

The terms "loweralkyl" or "alkyl" as used herein refer to straight or branched chain alkyl radicals containing from 1 to 4 carbon atoms including, but not limited to, methyl, ethyl, n-propyl, iso-propyl, n-butyl and the like.

The term "alkanoyloxy" as used herein refers to an alkyl group as previously defined appended to the parent molecular moiety through a carbonyl (—C(O)—O) group. Examples of alkanoyl include acetoxy, propionyloxy and the like.

The term "pharmaceutically acceptable salts, esters, and prodrugs" as used herein refers to those carboxylate salts, esters, and prodrugs of the compound of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. Pharmaceutically acceptable salts are well known in the art and refer to the relatively non-toxic, inorganic and organic acid addition salts of the compound of the present invention. For example, S. M. Berge, et al. describe pharmaceutically acceptable salts in detail in J. Pharmaceutical Sciences, 66: 1–19 (1977) which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Examples of pharmaceutically acceptable, non-toxic esters of the compounds of this invention include $C_1$ to $C_6$ alkanoyl esters wherein the alkanoyl group is a straight or branched chain. Esters of the compounds of the present invention may be prepared according to conventional methods.

The term "pharmaceutically acceptable prodrugs" as used herein refers to those prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexyl-carbodiimide) method, the active ester method (p-nitrophenyl ester method, N-hydroxy-succinic acid imide ester method, cyanomethyl ester method and the like), the Woodward reagent K method, the DCC-HOBT (1-hydroxy-benzotriazole) method and the like. Classical methods for amino acid condensation reactions are described in M. Bodansky, Y. S. Klausner and M. A. Ondetti, Peptide Synthesis, Second Edition, New York, 1976.

In another aspect of the present invention are disclosed pharmaceutical compositions comprising a therapeutically effective amount of a compound of the present invention formulated together with one or more non-toxic pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In a further aspect of the present invention is disclosed a method for treating or preventing bacterial infections in a human or lower mammal, comprising administering to a patient in need of such treatment or prophylaxis a therapeutically effective amount of a compound of the invention, for such time as is necessary to achieve a therapeutic effect. By a "therapeutically effective amount" of the compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compound of this invention administered to a human or other mammal in single or in divided doses can be in amounts, for example, from 0.01 to 50 mg/kg body weight or more usually from 0.0(1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound of this invention per day in multiple doses or in a single dose of from 10 mg to 1000 mg.

In yet another aspect of the present invention are disclosed processes useful in the preparation of the above compound represented in Schemes I–III.

In Scheme I, erythromycin D (1) is treated with an hydroxy protecting reagent (for example, an acid anhydride or acid chloride such as acetic anhydride or propionyl chloride or benzyl bromide) in the presence of a base (for example, a group I or group II hydroxide or carbonate or an organic base, such as potassium hydroxide, sodium hydroxide, lithium hydroxide or pyridine) to give a mixture of compounds 2 and 3 (wherein R is an hydroxy protecting group, for example acetyl or propionyl or benzyl) which are separable by column chromatography. Although not required, the 9-oxo group may be protected, for example as an oxime. Compound 3 is treated with an alkylating agent (for example, methyl iodide or methyl bromide, methyl p-toluenesulfonate, methyl methanesulfonate, dimethyl sulfate, ethyl iodide or ethyl bromide, ethyl p-toluenesulfonate, ethyl methanesulfonate, or diethyl sulfate) in the presence of a base (for example, potassium hydroxide, sodium hydroxide or lithium hydroxide) to provide the 6-O-alkyl compound 4 (wherein $R_1$ is loweralkyl). Removal of the hydroxy protecting groups of compound 4 (for example, hydrolysis using methanolic potassium carbonate or methanolic sodium or lithium or potassium hydroxide or hydrogenolysis in the case of benzyl ethers) affords the desired compound 5 (wherein $R_1$ is loweralkyl). If a 9-oximino protecting group has been used, it can be removed using for example, sodium hydrogen sulfite, sodium pyrosulfite, sodium thiosulfate, sodium sulfite, sodium metabisulfite, sodium dithionite, potassium hydrogen sulfite, potassium thiosulfate or potassium metabisulfite in a polar solvent containing an acid such as formic acid, acetic acid, propionic acid, oxalic acid, malonic acid or succinic acid. In a preferred embodiment, $R_1$ is methyl or ethyl.

A preferred embodiment of the process is shown in Scheme II. Erythromycin D is treated with acetic anhydride in the presence of sodium hydroxide or pyridine to afford a mixture of compounds 6 and 7 (wherein Ac is acetyl) which are separable by column chromatography. Compound 7 is treated with methyl iodide in the presence of sodium hydroxide to provide the 6-O-methyl compound 8. Hydrolysis of compound 8 in methanolic potassium carbonate affords the desired compound 9. Compound 9 may also be prepared from compound 1 by the procedures described without any intermediate purification or chromatography.

Scheme I

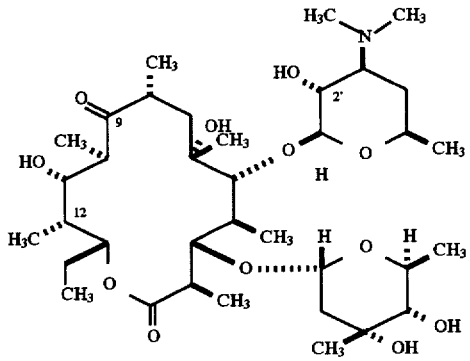

1

↓

-continued
Scheme I
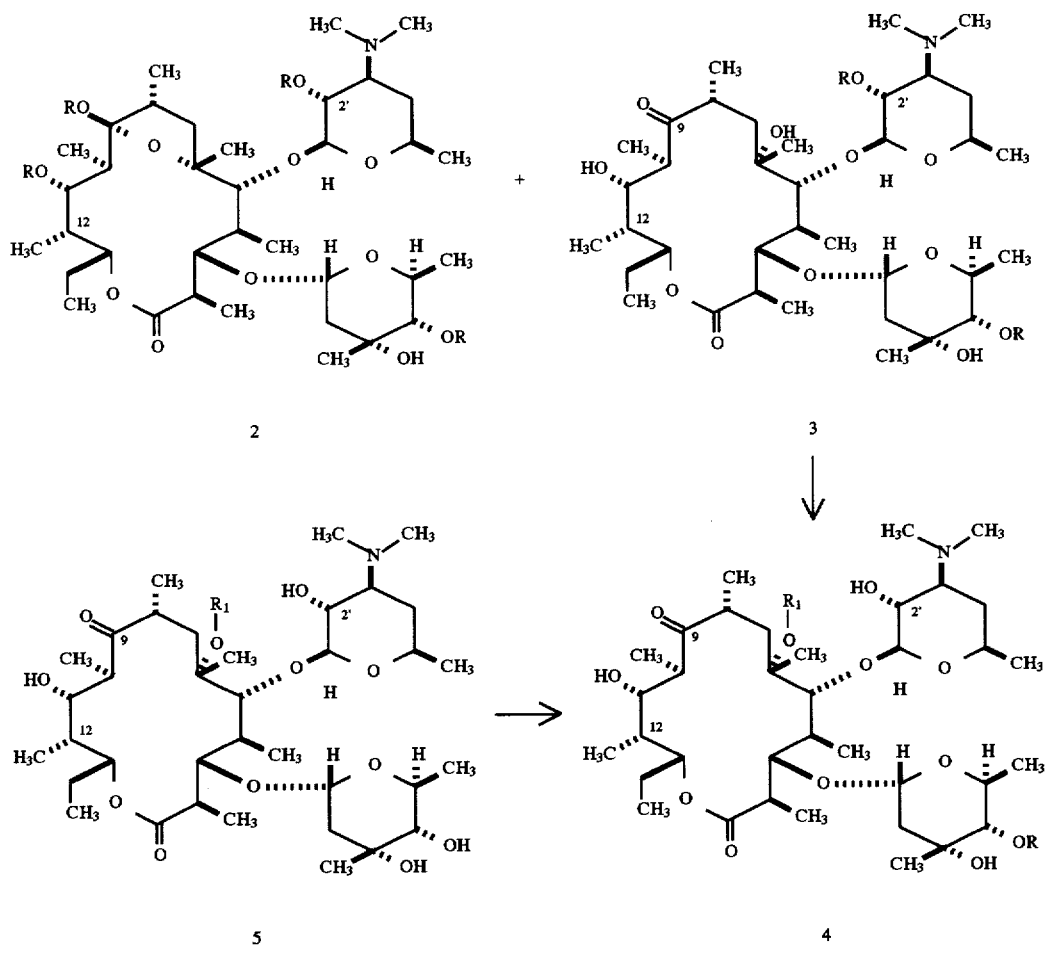
Scheme II
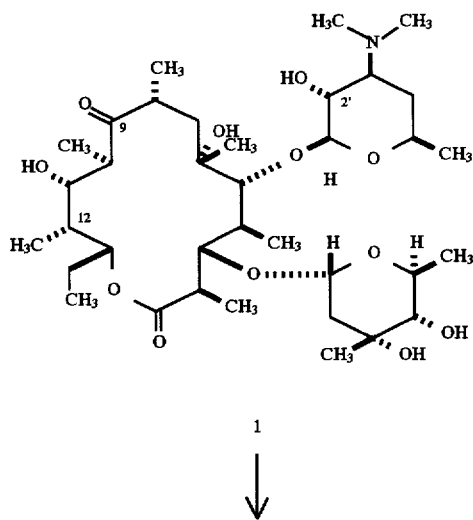

-continued
Scheme II

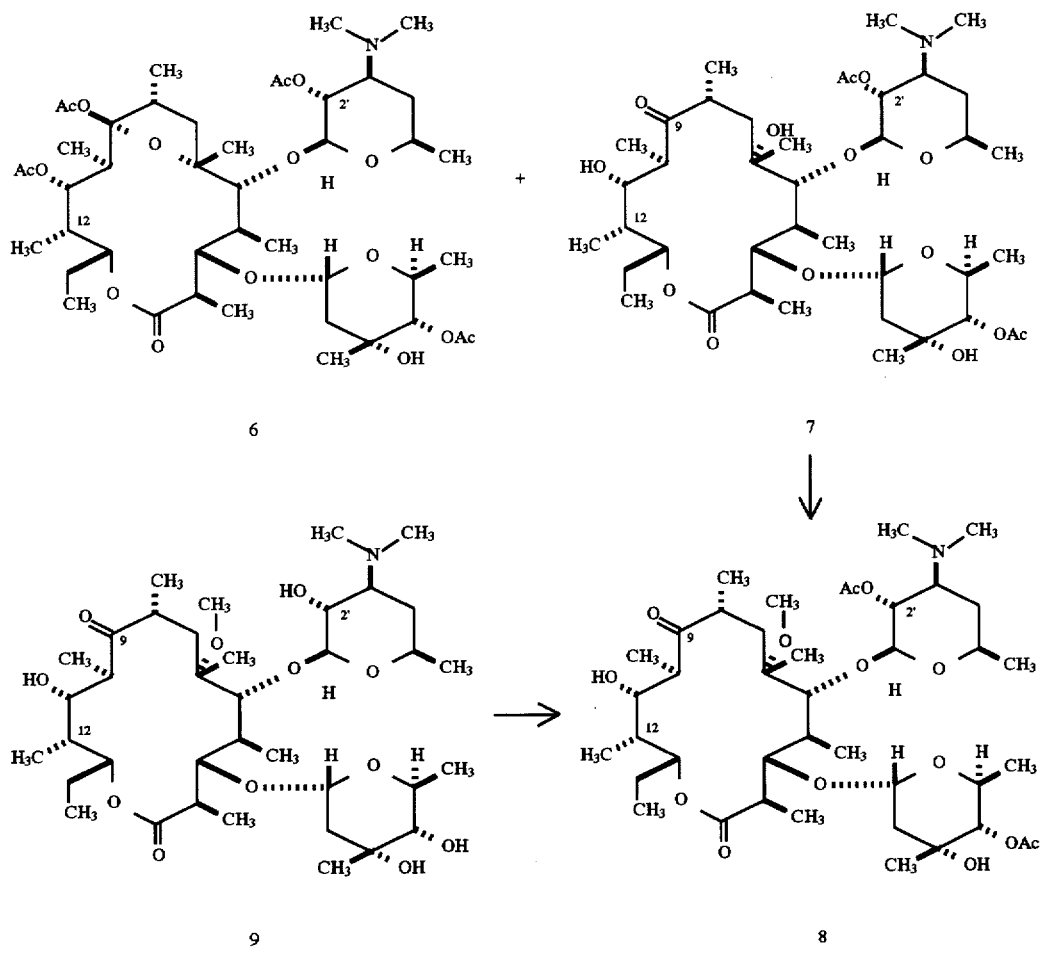

The present invention also comprises the use of 6-O-methylerythromycin D (9) as an intermediate in the preparation of 6-O-methylerythromycin A (10); this transformation is shown in Scheme III. The use of erythromycin D as an intermediate has the advantage that erythromycin D lacks the 12-hydroxyl group simplifying protection of the molecule and also avoiding the autoketalization reactions of erythromycin derivatives under mild acid conditions; these side reactions constitute a major undesirable side reaction (Kirst, H. A. and Sides, G. D., Antimicrobial Agents and Chemotherapy, 33, 1413 (1989)).

Scheme III

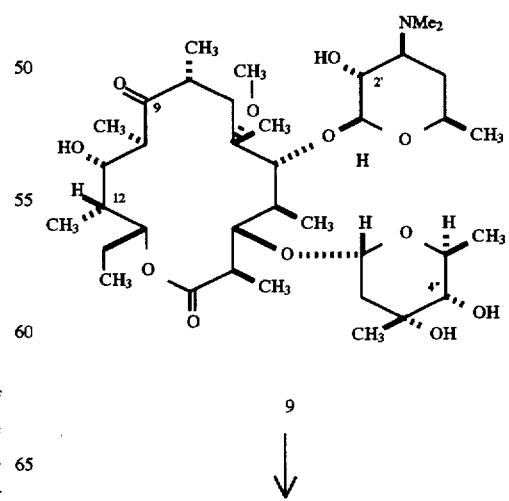

-continued
Scheme III

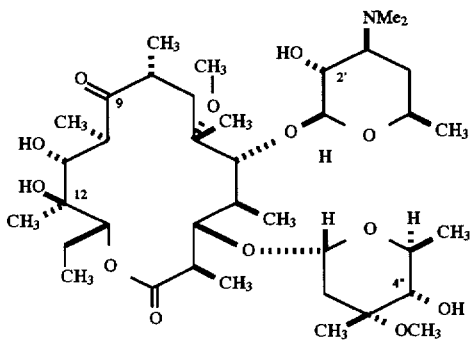

10

The above processes for preparing the compounds of the present invention will be better understood in connection with the following examples, which are intended as an illustration of and not a limitation upon the scope of the invention. The following abbreviations are used: DMF for dimethylformamide, Et$_3$N for triethylamine, EtOAc for ethyl acetate, EtOH for ethanol, MeI for methyl iodide, MeOH for methanol, and THF for tetrahydrofuran.

EXAMPLE 1

2',4"-O-Diacetyl-erythromycin D

To a suspension of 1.25 g (1.77 mmol) of erythromycin D and 1 mL (12.4 mmol) of pyridine in 13 mL of acetonitrile at 4° C. was added 1.17 mL (12.4 mmol) of acetic anhydride. The ice bath was removed, and the reaction mixture was allowed to warm to ambient temperature. After stirring for 45 hours, the reaction was quenched with 100 mL of 0.4N NaOH. The resultant emulsion was extracted with 2×50 mL of EtOAc. The combined organic extracts were washed with 50 mL of 0.4N NaOH and 50 mL of distilled water, dried and concentrated in vacuo. The residue obtained was flash chromatographed on silica gel eluting with 600:300:12 (v/v) hexane-acetone-triethylamine to afford 622.4 mg (44%) of the title compound. m.p. 118°–119° C. $^1$H NMR (CDCl$_3$, 300 MHz) δ 5.33 (ddd, 1H, J=9 Hz, 5 Hz, 0.8 Hz), 5.07 (br d, 1H, J=3.1 Hz), 4.75 (dd, 1H, J=111.1 Hz, 7.5 Hz), 4.63 (d, 1H, J=10.5 Hz), 4.47 (d, 1H, J=7.5 Hz), 4.25 (dd, 1H, J=9 Hz, 0.8 Hz), 4.16 (m, 1H), 3.75 (br d, 1H, J=9.2 Hz), 2.27 (s, 6H), 2.13 (s, 3H), 2.07 (s, 3H), 1.46 (s, 3H). $^{13}$C NMR (CDCl$_3$) δ 220.4, 175.7, 170.5, 170.0, 101.2, 98.7, 82.6, 82.5, 77.1, 75.5, 75.4, 71.6, 69.4, 69.2, 68.6, 63.8, 62.9, 44.7, 44.6, 41.0, 40.5, 39.7, 39.3, 38.8, 37.7, 30.7, 27.5, 25.4, 25.3, 21.3, 21.2, 20.8, 18.3, 18.0, 15.6, 11.2, 10.2, 9.1. MS (DCI/NH$_3$) m/e 788 (M+H)$^+$. IR (CDCl$_3$) 3510, 2970, 1735, 1695, 1458 cm$^{-1}$. HRMS Calcd for C$_{40}$H$_{70}$NO$_{14}$: 788.4796. Found: 788.4800.

EXAMPLE 2

2',4"-O-Diacetyl-6-O-methylerythromycin D

To the compound resulting from Example 1 (468 mg, 0.59 mmol) in 6 mL of DMF at 4° C. was added MeI (77.6 5 L, 1.25 mmol) followed by powder red KOH (70 mg, 1.25 mmol). The reaction was stirred at 4° C. for 20 minutes, and then quenched with a mixture of 20 mL of 2N NaOH and 10 mL of EtOAc. The phases were separated, and the organic phase was washed with 10 mL of distilled water and concentrated in vacuo. The residue obtained was flash chromatographed on silica gel eluting with a mixture of 600 mL of hexane, 300 mL of acetone and 12 mL of Et$_3$N to afford 294.5 mg (62%) of the title compound. m.p. 220°–221° C. $^1$H NMR (CDCl$_3$, 300 MHz) δ 5.38 (ddd, 1H, J=10.5 Hz, 4.8 Hz, 0.8 Hz), 5.13 (d, 1H, J=3.8 Hz), 4.72 (dd, 1H, J=10.8 Hz, 7.5 Hz), 4.63 (d, 1H, J=10.5 Hz), 4.49 (d, 1H, J=7.5 Hz), 4.16 (m, 1H), 3.90 (br d, 1H, J=9.2 Hz), 3.55 (br d, 1H, J=9.5 Hz), 3.05 (s, 3H), 2.26 (s, 6H), 2.12 (s, 3H), 2.04 (s, 3H), 1.39 (s, 3H). $^{13}$C NMR (CDCl$_3$) δ 219.9, 175.8, 170.3, 170.1, 100.8, 97.9, 80.8, 79.7, 78.8, 77.3, 75.2, 71.7, 69.6, 69.2, 68.0, 64.0, 62.7, 50.7, 45.2, 44.9, 40.9, 40.6, 40.1, 38.9, 38.4, 37.8, 31.0, 25.6, 21.5, 20.9, 20.2, 18.3, 18.2, 15.9, 10.5, 9.8, 9.2, 9.0. MS (FAB, Nitrobenzyl alcohol) m/e 802 (M)$^+$. IR (CDCl$_3$) 3495, 2970, 2940, 1735, 1690, 1459 cm$^{-1}$. Anal calcd for C$_{41}$H$_{71}$NO$_{14}$: C, 61.40; H, 8.92; N, 1.75. Found: C, 61.41; H, 8.74; N, 1.79.

EXAMPLE 3

6-O-Methylerythromycin D

To the compound resulting from Example 2 (425 mg, 0.53 mmol) in a mixture of 10 mL of MeOH and 2.5 mL of distilled water was added anhydrous K$_2$CO$_3$ (168 mg, 1.22 mmol). After 19 hours of stirring at ambient temperature, the reaction was diluted with 10 mL of distilled water, and the MeOH was removed in vacuo. The residue obtained was extracted with 2×25 mL of EtOAc, and the combined organic extracts were concentrated in vacuo to provide 374.8 mg (99%) of the title compound. m.p. 137° C. (of a sample crystallized from EtOH and water). $^1$H NMR (CDCl$_3$, 300 MHz) δ 5.38 (dd, 1H, J=10.6 Hz, 3.5 Hz), 5.06 (d, 1H, J=3.1 Hz), 4.27 (d, 1H, J=7.2 Hz), 3.91, 3.88 (d, 1H, J=9.1 Hz), 3.69, 3.64, 3.19, 3.51, 3.10 (s, 3H), 2.99, 2.92, 2.62, 2.44, 2.27 (s, 6H), 2.23, 2.02, 1.90, 1.84, 1.72, 1.71, 1.67, 1.64, 1.47, 1.46 (s, 3H), 1.37, 1.27, 1.25, 1.22, 1.12, 1.10, 0.98, 0.89, 0.83. $^{13}$C NMR (CDCl$_3$) δ 219.6, 175.9, 104.4, 98.7, 82.3, 82.1, 79.0, 76.4, 75.2, 70.9, 69.6, 69.4, 66.3, 65.5, 50.9, 45.2, 45.1, 40.4, 40.3, 40.2, 39.2, 39.0, 37.8, 28.4, 25.6, 25.5, 21.4, 19.9, 18.6, 18.4, 16.0, 10.5, 9.8, 9.1, 9.0. MS (DCI/NH$_3$) m/e 718 (M+H)$^+$. IR (CDCl$_3$) 3510, 2970, 1721, 1688, 1454 cm$^{-1}$. HRMS: Calcd for C$_{37}$H$_{68}$NO$_{12}$: 718.4741. Found: 718.4737.

EXAMPLE 4

Alternate Preparation of 6-O-Methylerythromycin D

To a solution of erythromycin D (1.0 g, 1.18 mmol) in 20 mL of anhydrous pyridine was added acetic anhydride (2 mL). The pale brown solution was stirred at ambient temperature for 2 days and then treated with 200 mL of diethyl ether. To the diluted solution was added 50 g of crushed ice and 10 mL of 2N NaOH. The organic phase was separated, dried over MgSO$_4$, filtered and concentrated in vacuo. The resultant oil was extracted with 3×10 mL portions of toluene which were combined and concentrated in vacuo to provide crude 2',4"-O-diacetyl-erythromycin D.

To the crude 2',4"-O-diacetyl-erythromycin D (0.9 g) prepared above dissolved in 11 mL of DMF and cooled to 4° C. was added methyl iodide (0.3 g, 2.1 mmol) followed by powdered KOH (0.1 g, 1.8 mmol). After stirring for 15 minutes, the reaction mixture was diluted with 50 mL of diethyl ether and quenched with 10 mL of 2N NaOH. The organic phase was washed with 2×10 mL of distilled water, dried over MgSO$_4$ and concentrated in vacuo to give 700 mg of crude 2',4"-O-diacetyl-6-O-methylerythromycin D.

The crude 2',4"-O-diacetyl-6-O-methylerythromycin D prepared above in 20 mL of MeOH was treated with 5 mL of 5% $K_2CO_3$ at ambient temperature. After 5 hours, the reaction mixture was diluted with 50 mL of diethyl ether and treated with 10 mL of 2N NaOH. The organic phase was washed with 2×15 mL of distilled water, dried over $MgSO_4$ and concentrated in vacuo to give 480 mg of crude title compound.

EXAMPLE 5

6-O-Ethylerythromycin D

The compound resulting from Example 1 is reacted by the procedures described in Example 2 substituting ethyl methanesulfonate for methyl iodide. The resulting 6-O-ethyl compound is deprotected by the procedures described in Example 3 to give the title compound.

In Vitro Assay of Antibacterial Activity

The 6-O-methyl erythromycin D compound of the present invention was assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35°–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each disk was read. The minimum inhibitory concentration (MIC) was defined as the lowest concentration of drug yielding no growth, a slight haze, or sparsely isolated colonies on the inoculum spot as compared to the growth control. The results of this assay, shown below in Table 1, support the conclusion that the 6-O-methyl erythromycin D compound of the invention is an effective antibacterial agent. 6-O-Methyl erythromycin D finds particular utility in being significantly more effective against *Pseudomonas aeruginosa* K799/61 and *Mycobaceterium smegmatis* ATCC 114.

TABLE 1

| | | MIC (µg/mL) | |
|---|---|---|---|
| ORGANISM | STRAIN | Erythromycin A | Example 3 |
| Staphylococcus aureus | ATCC 6538P | 0.2 | 0.39 |
| Staphylococcus aureus | A5177 | 1.56 | 3.1 |
| Staphylococcus aureus | A5278 | >100 | >100 |
| Staphylococcus aureus | 642a | 0.2 | 0.39 |
| Staphylococcus aureus | NCTC 10649 | 0.2 | 0.39 |
| Staphylococcus aureus | CMX 553 | 0.2 | 0.39 |
| Staphylococcus aureus | 1775 Cipro R | >100 | >100 |
| Staphylococcus epidermidis | 3519 | 0.2 | 0.39 |
| Enterococcus faecium | ATCC 8043 | 0.05 | 0.1 |
| Streptococcus bovis | A5169 | 0.02 | 0.01 |
| Streptococcus agalactiae | 508 | 0.05 | 0.05 |

TABLE 1-continued

| | | MIC (µg/mL) | |
|---|---|---|---|
| ORGANISM | STRAIN | Erythromycin A | Example 3 |
| Streptococcus pyogenes | EES61 | 0.05 | 0.05 |
| Streptococcus pyogenes | 930 const | >100 | >100 |
| Streptococcus pyogenes | 2548 induc | 6.2 | 3.1 |
| Micrococcus luteus | ATCC 9341 | 0.05 | 0.05 |
| Micrococcus luteus | 4698 | 0.01 | 1.56 |
| Escherichia coli | Juhl | 50 | >100 |
| Escherichia coli | SS | 0.2 | 0.39 |
| Escherichia coli | DC-2 | 50 | >100 |
| Escherichia coli | H560 | 2.5 | >100 |
| Escherichia coli | KNK 437 | 50 | >100 |
| Enterobacter aerogenes | ATCC 13048 | 100 | >100 |
| Klebsiella pneumoniae | ATCC 8045 | 50 | >100 |
| Providencia stuartii | CMX 640 | >100 | >100 |
| Pseudomonas aeruginosa | BMH10 | >100 | >100 |
| Pseudomonas aeruginosa | A5007 | >100 | >100 |
| Pseudomonas aeruginosa | K799/WT | >100 | >100 |
| Pseudomonas aeruginosa | K799/61 | >100 | 1.56 |
| Acinetobacter calcoaceticus | CMX 669 | 12.5 | >100 |
| Pseudomonas aeruginosa | 5263 | >100 | >100 |
| Pseudomonas aeruginosa | 2862 | >100 | >100 |
| Candida albicans | CCH 442 | | >100 |
| Mycobaceterium smegmatis | ATCC 114 | 12.5 | 0.78 |
| Nocardia asteroides | ATCC 9970 | 0.05 | 0.05 |

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound having the formula

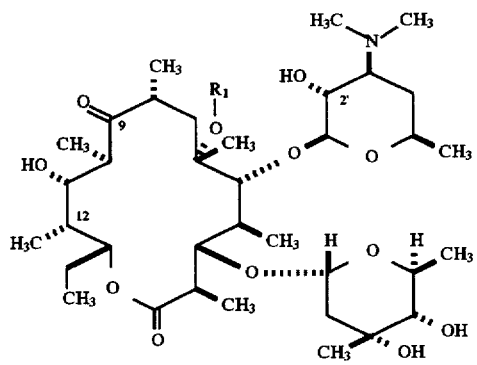

wherein $R_1$ is loweralkyl, or a pharmaceutically acceptable salt, ester or prodrug thereof.

2. A compound according to claim 1 wherein $R_1$ is methyl.

3. A compound of the formula

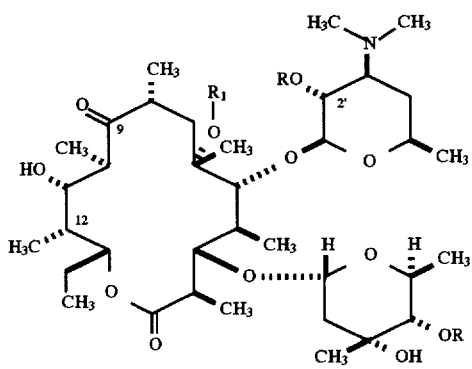

wherein R is an hydroxy protecting group and $R_1$ is loweralkyl.

4. A compound according to claim 3 wherein $R_1$ is methyl.
5. A compound according to claim 3 wherein R is acetyl, propionyl or benzyl.
6. A compound according to claim 3 wherein R is acetyl and $R_1$ is methyl.
7. A process for the preparation of 6-O-loweralkyl erythromycin D comprising protecting the 2' and 4"-positions of erythromycin D with hydroxy protecting groups, alkylating the 6-hydroxy group, and de-protecting the 2' and 4"-positions.
8. A process for the preparation of a compound of the formula:

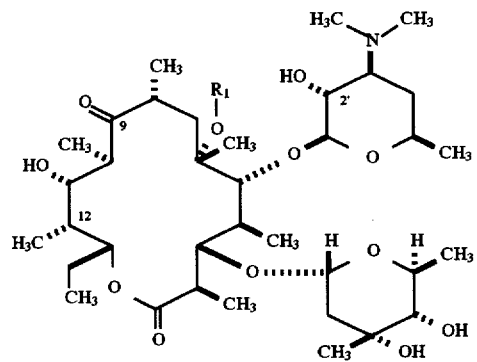

wherein $R_1$ is loweralkyl comprising treating a compound of the formula:

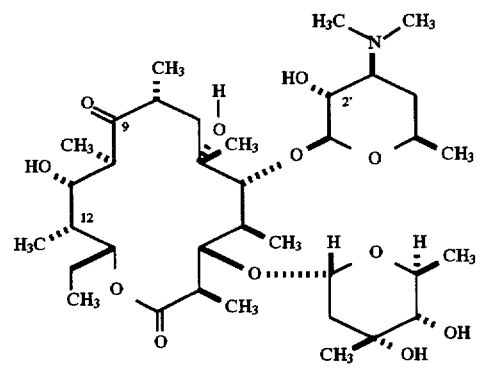

with an hydroxy protecting reagent selected from acetic anhydride, propionyl chloride and benzyl bromide in the presence of a base selected from the group consisting of potassium hydroxide, sodium hydroxide and lithium hydroxide to give a compound of the formula:

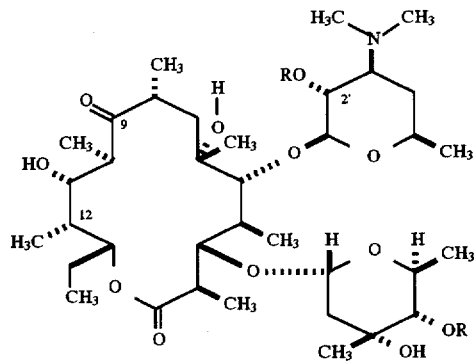

wherein R is acetyl, propionyl or benzyl;

treating said compound with an alkylating agent selected from the group consisting of methyl iodide, methyl bromide, methyl p-toluenesulfonate, methyl methanesulfonate, dimethylsulfate, ethyl iodide, ethyl bromide, ethyl p-toluenesulfonate, ethyl methanesulfonate, and diethylsulfate to give a compound of the formula:

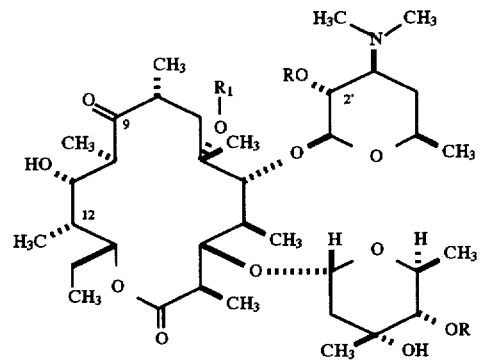

wherein $R_1$ is methyl or ethyl and R is acetyl, propionyl or benzyl; and treating said compound with ethanolic or methanolic potassium carbonate, sodium hydroxide, lithium hydroxide or potassium hydroxide or catalytic hydrogenation.

9. The process according to claim 8 wherein the hydroxy-protecting reagent is acetic anhydride and the base is sodium hydroxide to give R=acetyl, the alkylating reagent is methyl iodide to give $R_1$=methyl, and deprotecting with methanolic potassium carbonate.

10. A pharmaceutical composition comprising a therapeutically effective amount of a compound according to claim 1 and a pharmaceutically acceptable carrier.

11. A method for treating bacterial infections in a human or other animal, comprising administering to a patient in need of such treatment a therapeutically effective amount of a compound according to claim 1.

* * * * *